US009554784B2

United States Patent
Vidlund

(10) Patent No.: US 9,554,784 B2
(45) Date of Patent: Jan. 31, 2017

(54) BIORESORBABLE TIP WITH LOW FORCE RELEASE AND METHODS

(71) Applicant: St. Jude Medical Puerto Rico LLC, Caguas, PR (US)

(72) Inventor: Robert M. Vidlund, Forest Lake, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 232 days.

(21) Appl. No.: 13/744,099

(22) Filed: Jan. 17, 2013

(65) Prior Publication Data

US 2013/0190812 A1    Jul. 25, 2013

Related U.S. Application Data

(60) Provisional application No. 61/590,027, filed on Jan. 24, 2012.

(51) Int. Cl.
    *A61B 17/08*     (2006.01)
    *A61D 1/00*      (2006.01)
    *A61B 17/00*     (2006.01)

(52) U.S. Cl.
    CPC .. *A61B 17/0057* (2013.01); *A61B 2017/00623* (2013.01); *A61B 2017/00654* (2013.01); *A61B 2017/00659* (2013.01)

(58) Field of Classification Search
    CPC .............. A61B 17/0057; A61B 17/00491; A61B 17/3431; A61B 2017/00637; A61B 2017/0065; A61B 2017/00654; A61B 2017/0004; A61B 2017/00495; A61F 2/00; A61L 2400/04; A61L 24/0042; A61M 2025/0233; A61M 25/04

USPC ....... 606/139, 191, 192, 213, 214, 215, 216, 606/228; 604/57, 103.01, 264

See application file for complete search history.

(56) References Cited

U.S. PATENT DOCUMENTS

| 5,419,765 A * | 5/1995 | Weldon .............. A61B 17/0057 604/507 |
| 5,922,022 A * | 7/1999 | Nash et al. .................. 623/1.35 |
| 7,850,710 B2 | 12/2010 | Huss |
| 8,128,652 B2 | 3/2012 | Paprocki |

(Continued)

FOREIGN PATENT DOCUMENTS

| WO | 9933403 A1 | 7/1999 |
| WO | 2005055801 A2 | 6/2005 |
| WO | 2006115904 A2 | 11/2006 |

OTHER PUBLICATIONS

Tegels et al., U.S. Appl. No. 61/589,930, filed Jan. 24, 2012.

(Continued)

*Primary Examiner* — Katherine M Shi
*Assistant Examiner* — Mohamed Gabr
(74) *Attorney, Agent, or Firm* — Holland & Hart

(57) ABSTRACT

A vascular closure system includes an expandable anchor, a sealing material, a sealing tip, and a sealing tip release member. The expandable anchor is temporarily positioned through a vessel puncture within a vessel. The sealing material is positioned outside of the vessel and configured to seal the vessel puncture. The sealing tip is positioned distal of the anchor and releasable within the sealing material upon removal of the anchor and sealing tip through the sealing material. The sealing tip release member is operable to release the sealing tip without application of a tactile force.

6 Claims, 14 Drawing Sheets

(56) References Cited

U.S. PATENT DOCUMENTS

| | | |
|---|---|---|
| 8,262,693 B2 | 9/2012 | Pai et al. |
| 8,333,787 B2 | 12/2012 | Pipenhagen et al. |
| 8,506,592 B2 | 8/2013 | Killion et al. |
| 2009/0171282 A1* | 7/2009 | Pipenhagen et al. .... 604/103.01 |
| 2010/0211000 A1* | 8/2010 | Killion et al. .................. 604/57 |
| 2011/0166595 A1* | 7/2011 | Vidlund ............. A61B 17/0057 606/213 |
| 2011/0282383 A1 | 11/2011 | Vidlund et al. |
| 2013/0006299 A1 | 1/2013 | Pipenhagen et al. |

OTHER PUBLICATIONS

Tegels et al., U.S. Appl. No. 61/590,000, filed Jan. 24, 2012.
Notification of Transmittal of the International Search Report and the Written Opinion of the International Searching Authority, or the Declaration for PCT International Application No. PCT/US2013/021798, mailed Apr. 2, 2013, (15 pp.).

* cited by examiner

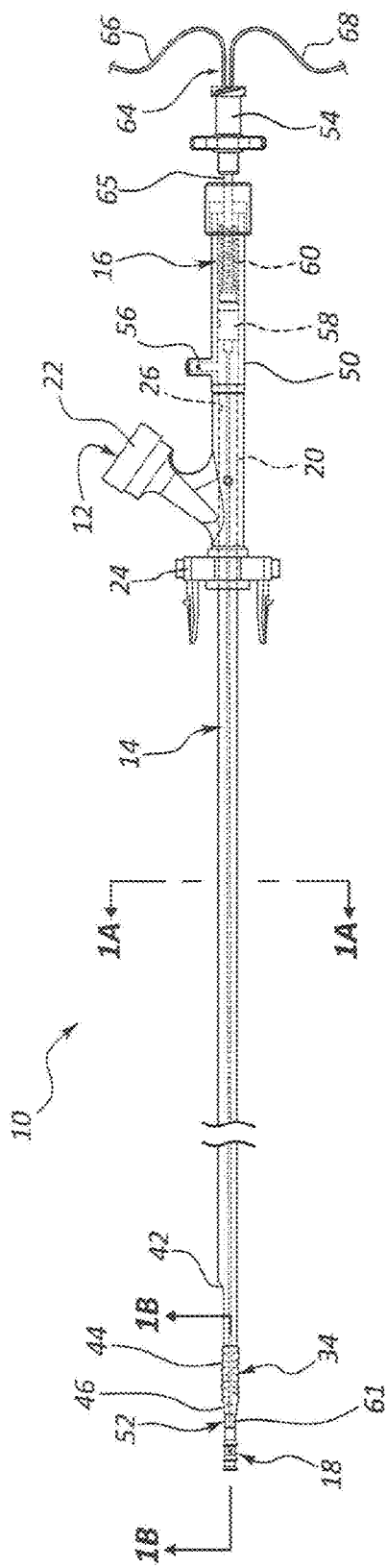

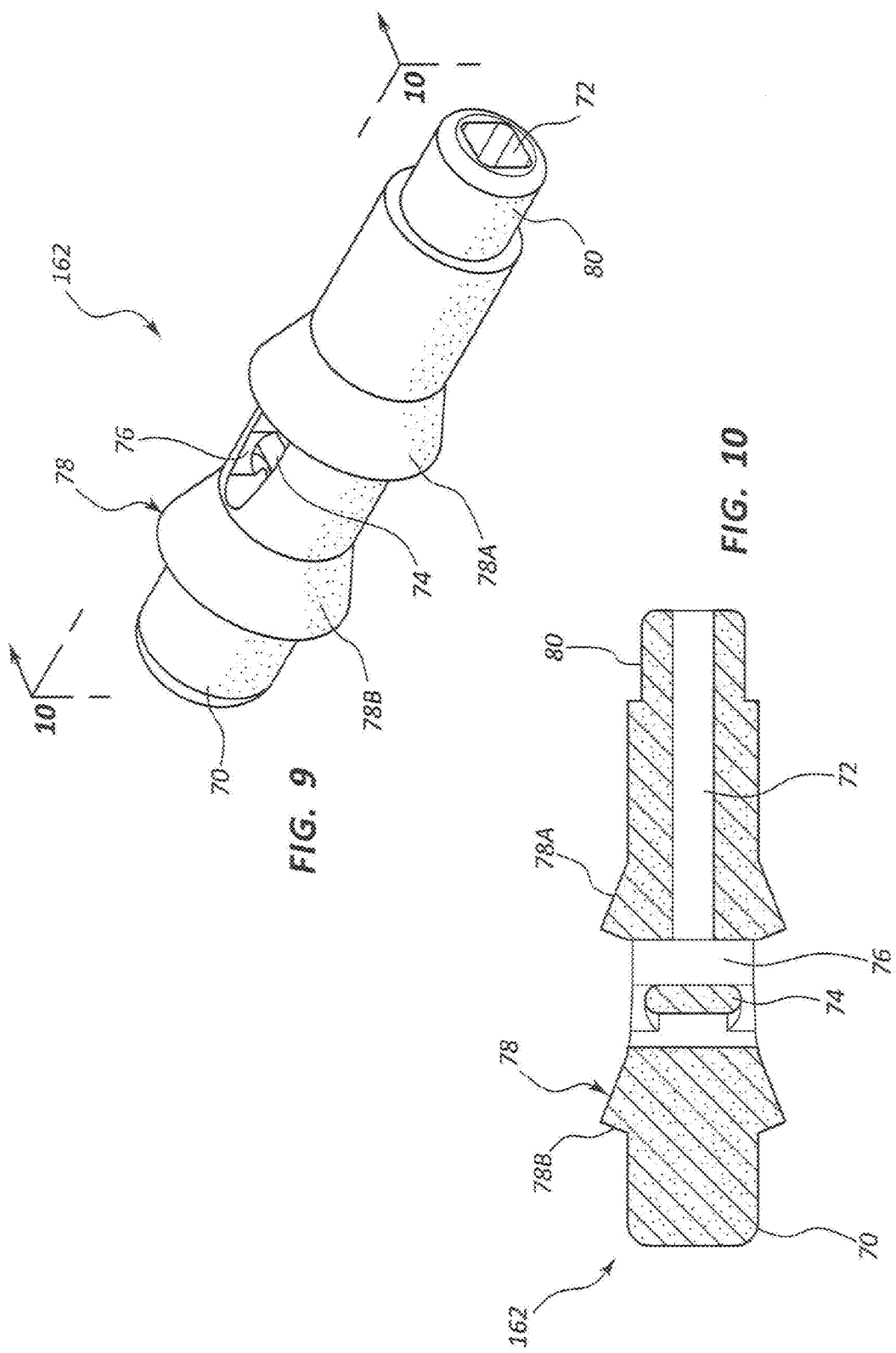

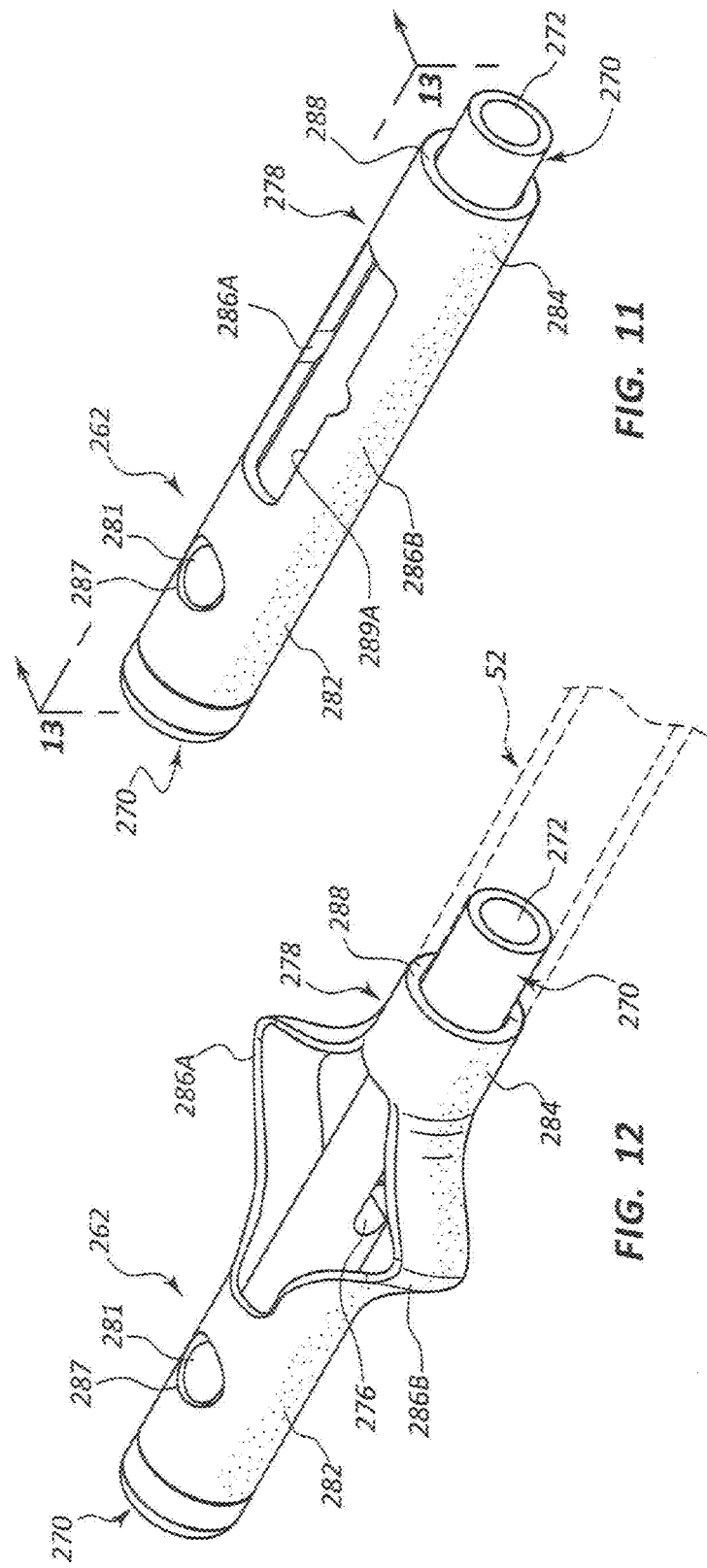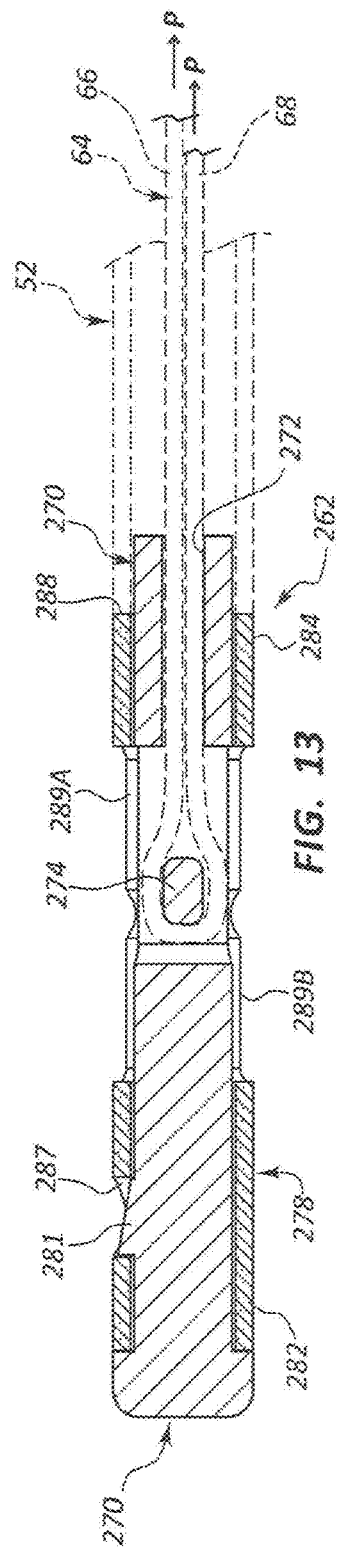

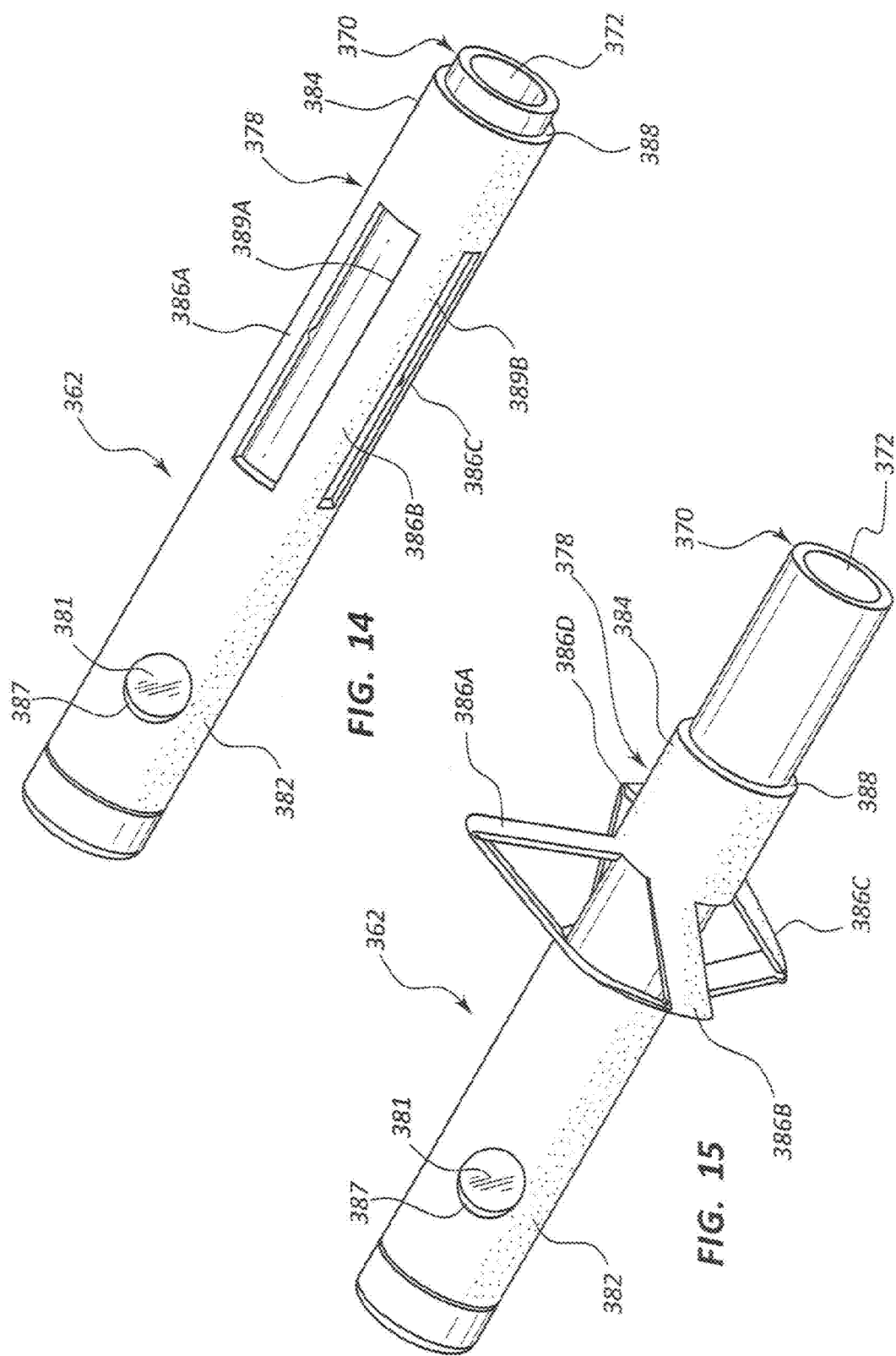

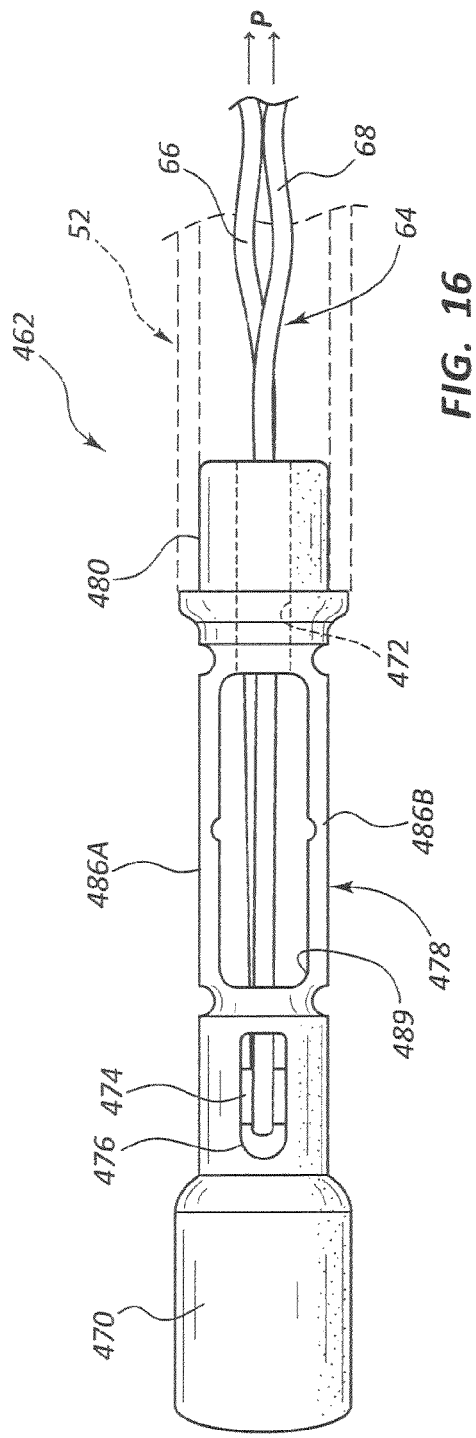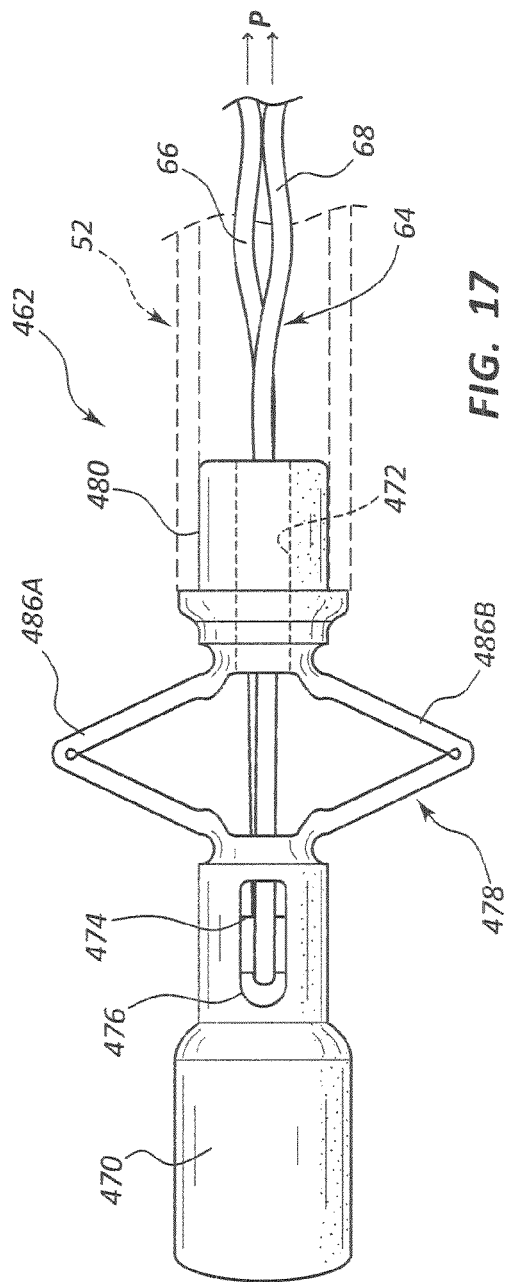

BIORESORBABLE TIP WITH LOW FORCE RELEASE AND METHODS

CROSS-REFERENCE TO RELATED APPLICATION

This application claims the benefit of the filing date of U.S. Provisional Application No. 61/590,027, filed Jan. 24, 2012, and entitled BIORESORBABLE TIP WITH LOW FORCE RELEASE AND METHODS, the disclosure of which is incorporated, in its entirety, by this reference.

TECHNICAL FIELD

The present disclosure relates generally to methods and systems for sealing tissue punctures, and more particularly, to methods and systems for depositing a secondary sealing member to seal tissue punctures.

BACKGROUND

Various surgical procedures are routinely carried out intravascularly or innaluminally. For example, in the treatment of vascular disease, such as arteriosclerosis, it is a common practice to access the artery and insert an instrument (e.g., a balloon or other type of catheter) to carry out a procedure within the artery. Such procedures usually involve the percutaneous puncture of the artery so that an insertion sheath may be placed in the artery and thereafter instruments (e.g., catheters) may pass through the sheath to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices.

While there are a variety of prior art devices and techniques for closing such punctures, one method includes temporarily sealing the tissue puncture intravascularly using an inflation balloon. A sealing material may be delivered to an outer surface of the tissue to seal the tissue puncture while the temporary seal from the balloon is maintained. Removing the collapsed balloon through the sealing material may leave a tract through the sealing material. Challenges may exist in closing the tract.

SUMMARY

One aspect of the present disclosure relates to a vascular closure system that includes an expandable anchor, a sealing material, a sealing tip, and a sealing tip release member. The expandable anchor is temporarily positioned through a vessel puncture within a vessel. The sealing material is disposed outside of the vessel and configured to seal the vessel puncture. The sealing tip is positioned distal of the anchor and releasable within the sealing material upon removal of the anchor and sealing tip through the sealing material. The sealing tip release member is operable to release the sealing tip without application of a tactile force.

The sealing tip release member may include a filament that at least partially wraps around a filament anchor of the sealing tip, and unwinding the filament from the filament anchor releases the sealing tip. The sealing tip may include a tip securement member expandable within the sealing material. The sealing tip release member may include a filament connected to the sealing tip, wherein applying an axially directed force to the filament operates the tip securement member into an expanded position. The anchor may include an expandable balloon structure. The sealing tip may include a bioresorbale material. The sealing tip may include first and second portions, and relative axial movement between the first and second portions while assembled together expands the sealing tip within the sealing material. The sealing tip may include at least one tip securement member extending radially outward from the sealing tip to anchor the sealing tip within the sealing material.

Another aspect of the present disclosure relates to a vascular closure device that includes an anchor and a detachable sealing tip assembly having a sealing tip and a filament. The anchor is positionable through a vessel puncture and configured to temporarily seal the vessel puncture. The sealing tip is positionable distal of the anchor. The filament extends proximally from the sealing tip and is operable to unwind from the sealing tip to release the sealing tip from the vascular closure device to seal the vessel puncture after removal of the anchor from the vessel puncture.

The vascular closure device may also include a sealing material positionable outside of the vessel puncture to seal the vessel puncture, and the sealing tip is released within the sealing material. The sealing material may be a bioadhesive, and removal of the anchor through the bioadhesive forms a tract through the bioadhesive that is filled with the sealing tip. The sealing tip may include a base portion and a tip securement portion that extends radially outward from the base portion to anchor the sealing tip. The sealing tip may include a base portion and a tip securement portion, and relative axial movement between the base portion and the tip securement portion expands the tip securement portion.

Another aspect of the present disclosure relates to a method of closing a vascular opening in a vessel wall. The method includes providing a vascular closure device having an anchor member, a sealing material, a sealing tip, and a release member, advancing the anchor member and sealing tip through the vessel opening, and expanding the anchor and contacting the anchor against an inner surface of the vessel adjacent to the vessel opening. The method also includes positioning the sealing material against an outer surface of the vessel adjacent to the vessel opening, withdrawing the anchor through the vessel opening and sealing material, positioning the sealing tip in the sealing material, and operating the release member to release the sealing tip within the sealing material without application of a tensile force.

The tip release member may include a filament that wraps around a portion of the sealing tip, and operating the tip release member includes unwrapping the filament from the portion of the sealing tip. The sealing tip may also include a tip securement member, and applying tension in the filament expands the tip securement member within the sealing material. The sealing tip may include a tip securement member that extends radially backyard from the sealing tip, and the method includes anchoring the tip securement member in the sealing material prior to operating the release. The tip securement member may include at least three expandable members that extend radially outward upon operating the release member. The anchor may include an inflatable balloon that is inflated through an inflation lumen, and the release member extends through the inflation lumen. The release member may extend into an interior of the sealing tip, and operating the release member includes removing the release member from within the sealing tip.

The foregoing and other features, utilities, and advantages of the invention will be apparent from the following detailed description of the invention with reference to the accompanying drawings.

BRIEF DESCRIPTION OF THE DRAWINGS

The accompanying drawings illustrate various embodiments of the present disclosure and are a part of the specification. The illustrated embodiments are merely examples of the present disclosure and do not limit the scope of the invention.

FIG. 1 is a side view of an example vascular closure device in accordance with the present disclosure.

FIG. 1A is a cross-sectional view of the vascular closure device of FIG. 1 taken along cross-section indicators 1A-1A.

FIG. 9 is a perspective view of another example sealing tip in accordance with the present disclosure for use with the vascular closure device of FIG. 1.

FIG. 10 is a cross-sectional view of the sealing tip of FIG. 9.

FIG. 11 is a perspective view of another example scaling tip in accordance with the present disclosure for use with the vascular closure device of FIG. 1.

FIG. 12 is a perspective view of the sealing tip of FIG. 11 in an expanded position.

FIG. 13 is a cross-sectional view of the sealing tip of FIG. 11.

FIG. 14 is a perspective view of another example sealing tip in accordance with the present disclosure for use with the vascular closure device of FIG. 1.

FIG. 15 is a perspective view of the sealing tip of FIG. 14 in an expanded position.

FIG. 16 is a side view of another example sealing tip in accordance with the present disclosure for use with the vascular closure device of FIG. 1.

FIG. 17 is a side view of the sealing tip of FIG. 16 in an expanded position.

Throughout the drawings, identical reference numbers designate similar, but not necessarily identical, elements.

DETAILED DESCRIPTION

Figure 1B:
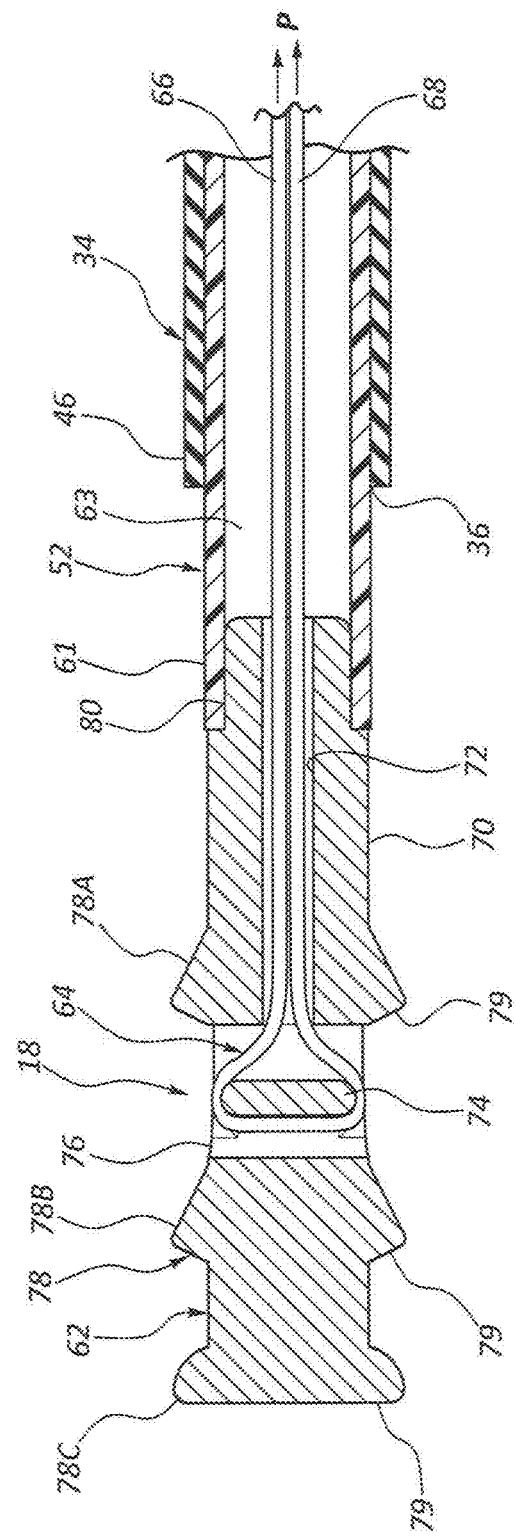
FIG. 1B is a cross-sectional view of a distal end portion of the vascular closure device of FIG. 1 taken along cross-section indicators 1B-1B.

The systems disclosed he/nit may be used to close or seal percutaneous punctures made through the body tissue of a patient to gain access to a body cavity of a patient. Access through these percutaneous punctures allows a physician to carry out various procedures in or through the body cavity for examination, surgery, treatment and the like. While not meant to be limiting, the systems are illustrated being used to seal percutaneous punctures that provide access to blood vessels in patients for various procedures. It will be appreciated that the systems are applicable to other procedures requiring sealing of a puncture through body tissue into a cavity including, for example, laparoscopic surgery and other microscopic surgery techniques using a relatively small incision.

The general structure and function of tissue closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as pictures or incisions in blood vessels, ducts or lumens, gall bladders, livers, hearts, etc.

As used in this specification and the appended claims, the terms "engage" and "engagable" are used broadly to mean interlock, mesh, or contact between two structures or devices. Likewise "disengage" or "disengagable" means to remove or capable of being removed from interlock, mesh, or contact. A "tube" is an elongated device with a passageway. The passageway may be enclosed or open (e.g., a trough). A "lumen" refers to any open space or cavity in a bodily organ, especially in a blood vessel. The words "including" and "having," as well as their derivatives, as used in the specification, including the claims, have the same meaning as the word "comprising."

An exemplary embodiment of the present disclosure includes a vascular closure device having a detachable sealing tip. The vascular closure device is used with a sheath that provides access through a vessel puncture and into an inner lumen of the vessel. The vascular closure device may include a delivery tube having a dual lumen construction wherein one lumen is used to deliver a bioadhesive sealant to the tissue puncture and the other lumen is used as an inflation lumen for delivering inflation fluid to an inflatable balloon anchor positioned at a distal end of the vascular closure device. The inflation lumen may also be configured for passage of an inner tube that helps carry the detachable sealing tip. The inner tube may be part of a balloon location device that helps monitor an inflation condition of the balloon anchor. The inner tube may be connected to the balloon and move axially as the balloon is inflated to provide a visual indication of, for example, an inflation pressure, size or shape of the balloon anchor.

The inner tube may also be used to deliver a secondary bioadhesive sealant to the tissue puncture in addition to carrying the detachable sealing tip. The secondary bioadhesive sealant may be used to help seal a tract defined in the first bioadhesive sealant upon removal of the delivery tube from the vessel and tissue puncture. A distal end of the inner tube may extend distal of the balloon. A proximal end of the inner tube may extend proximal to the housing of the balloon location device. An inner tube manifold may be mounted to a proximal end of the inner tube to connect the inner tube with a source of secondary bioadhesive sealant.

The detachable sealing tip may be carried on the inner tube at a position distal of the balloon anchor. The detachable sealing tip may be part of an assembly that includes the detachable sealing tip and a release member. The release member may provide a low or no tensile force release of the detachable sealing tip. In one example, the release member includes a filament that wraps around a portion of the detachable sealing tip to maintain the detachable sealing tip attached to the vascular closure device during initial operation of the vascular closure device to deliver a sealing material (e.g., a bioadhesive sealant) to the vessel puncture. The filament may be unwound from the detachable sealing tip to permit release of the detachable sealing tip. In one example, the filament extends through the inner tube to the detachable sealing tip and includes first and second free ends that extend proximally from the vascular closure device. Tension is applied in both of the free ends to maintain the detachable sealing tip assembled with the rest of the vascular closure device. Releasing the detachable sealing tip includes releasing tension in one of the free ends of the filament while pulling (maintaining tension) in the other free end of the filament to unwind or unwrap the filament from the detachable sealing tip. The detachable sealing tip may be released with application of relatively little force to the vascular closure device.

Typically, the detachable sealing tip is released within the sealing material upon retraction of the vascular closure device from the vessel puncture. The detachable sealing tip may be configured to detach from the vascular closure device within the sealing material after the balloon anchor has been withdrawn through the sealing material. The detachable sealing tip may be operated into an expanded position prior to being detached within the sealing material. The detachable sealing tip may include an assembly of parts, which when moved relative to each other (e.g., by application of an axial force applied by the release member (e.g., filament)), move one of the parts into an expanded position that provides additional anchoring within the sealing material to help hold the detachable sealing tip within the sealing material. In other embodiments, a single piece detachable sealing tip may be expandable upon application of an axial force.

Using a filament wrapped around a portion of a detachable sealing tip as a low or no tensile force release member for a detachable tip assembly is only one of many possible ways to release a detachable sealing tip using relatively low tensile force (e.g., less than 1 lb. force). Further, there may be other ways to route a release member (e.g., filament) to a detachable sealing tip beside through an inner tube of a balloon location device such as the one illustrated in the attached figures.

The phrases "low tactile force," "no tactile force," and "without application of a tactile force" as they relate to releasing the detachable sealing tip from the vascular closure device may mean little force or no force (e.,g., in the range of less than 1 lb. force) applied in an axial direction. Alternatively, these phrases may mean removing a suture from contact with the detachable seal g tip by unwrapping the structure from around an anchor portion of the detachable sealing tip, by applying a force in a lateral direction to the detachable sealing tip, and providing sliding movement of the suture as it unwraps or unwinds from the detachable sealing tip.

Figure 2:
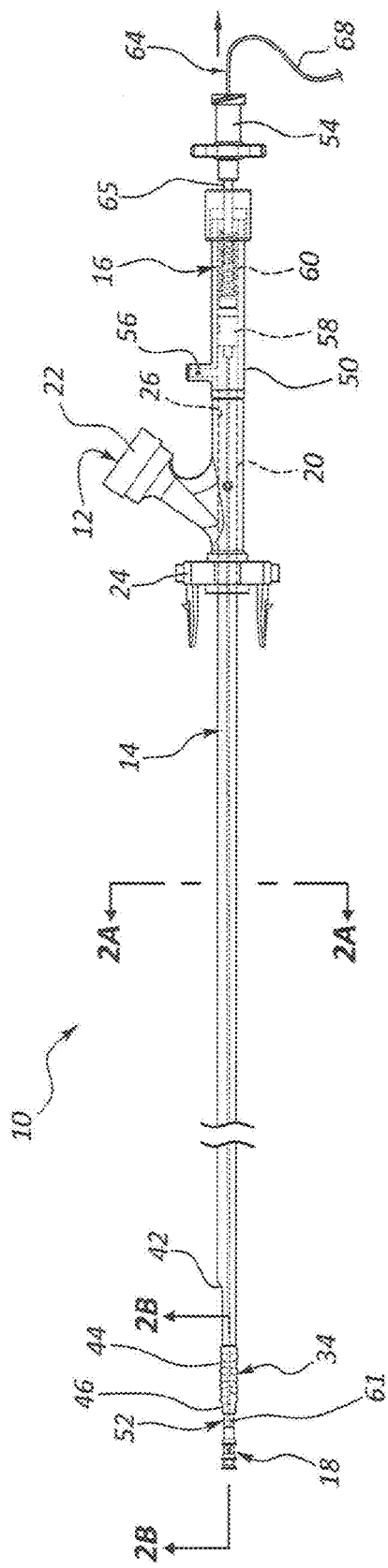
FIG. 2 is a side view of the vascular closure device of FIG. 1 with a sealing tip being released.
Figure 2A:
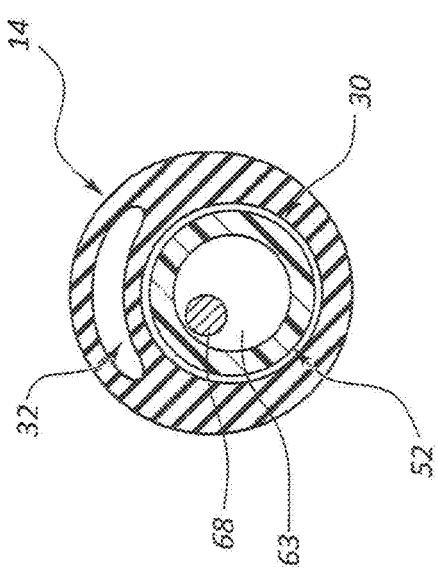
FIG. 2A is a cross-sectional view a vascular closure device of FIG. 2 taken along cross-section indicators 2A-2A.
Figure 3:
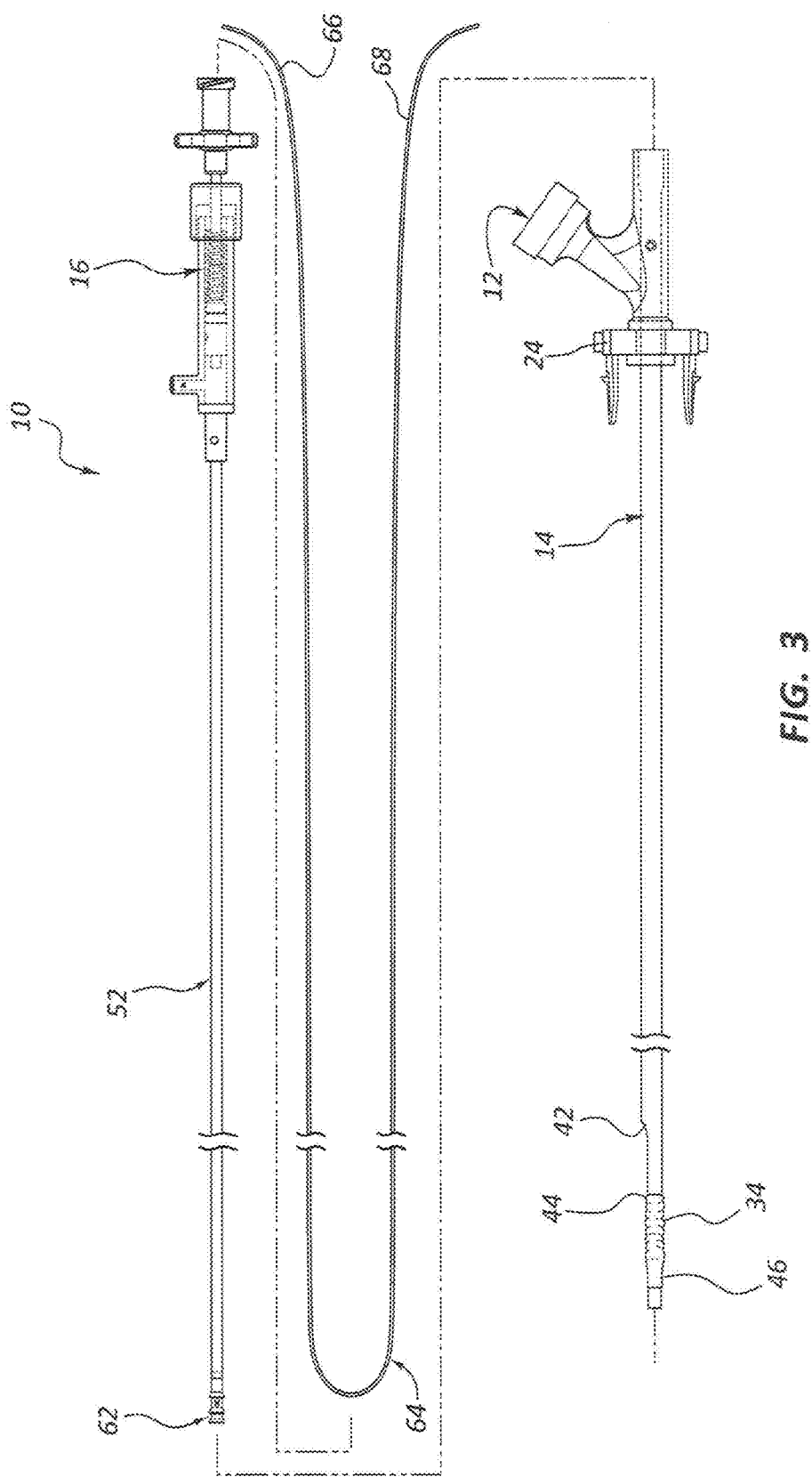
FIG. 3 is an exploded view of the vascular closure device of FIG. 1.
Figure 4:
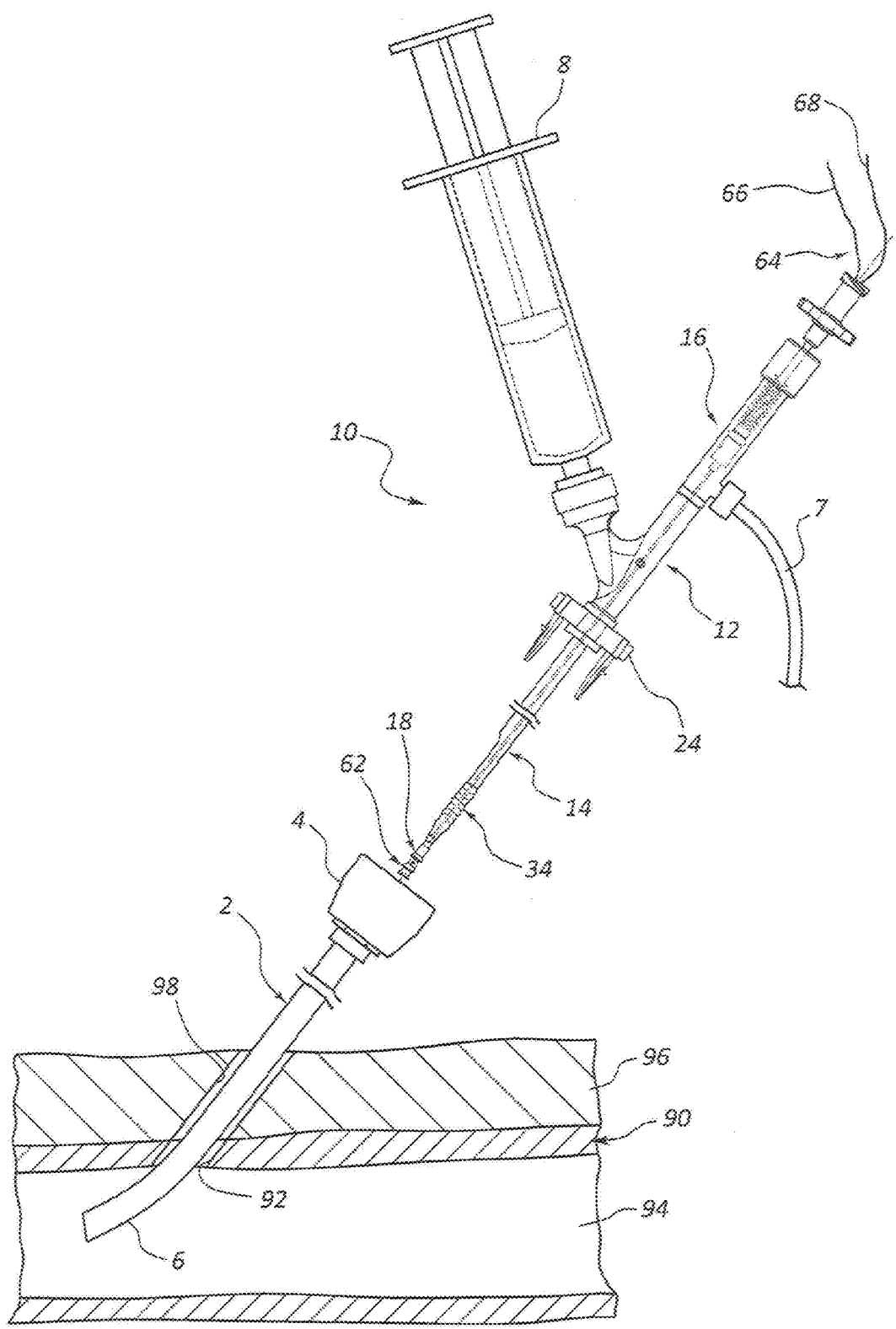
FIGS. 4-8 illustrate use of the vascular closure device of FIG. 1 with a sheath to seal a vessel puncture in accordance with the present disclosure.

Referring now to FIGS. 1-3, an example vascular closure device 10 is shown and describe. The vascular closure device 10 includes a manifold 12, a delivery tube 14, a balloon location device 16, and a detachable tip assembly 18. The vascular closure device 10 may be used with a sheath 2 as shown in FIGS. 4-8 for treatment of a vessel puncture 92 extravascularly. Operation of the vascular closure device 10 may be generally referred to as extravascular closure of vessel puncture 92. The principles disclosed here and related to the vascular closure device 10 may be applicable to other types and methods of closuring openings in any tissue.

The manifold 12 may include a delivery device passage 20, an injection port 22, and a latch or connector 24 (see FIG. 3). The delivery device passage 20 may include a proximal opening or seat 26 sized to receive a distal end of the balloon location device 16. The delivery tube 14 may be secured to the manifold 12 within the delivery device passage 20 (see FIG. 1). In one example, the delivery tube 14 is connected to the manifold 12 using, for example, an adhesive, sealant, bonding agent, or other device or structure to retain the delivery tube 14 within the delivery device passage. Details concerning example manifolds that may be used as manifold 12 are disclosed in U.S. Patent Application No. 61/589,930 filed on 24 Jan. 2012 and entitled BIOADHESIVE DELIVERY CATHETER MANIFOLD WITH MIXING FIXTURE AND METHODS, which application is incorporated herein in its entirety by this reference.

A passage leading from the injection port 22 intersects with the delivery device passage 20. When the delivery tube 14 and balloon location device 16 are mounted to the manifold 12, one of the lumens of the delivery tube 14 is connected in fluid communication with the injection port 22 to receive a volume of sealing material (e.g., a bioadhesive sealant), and the other lumen of the delivery tube 14 is connected in fluid communication with a source of inflation fluid that is connected to the balloon location device 16.

Latch 24 is configured to releasably attach the vascular closure device 10 to the sheath 2 to limit axial movement of the vascular closure device 10 relative to the sheath 2. In operation, the sheath 2 is first positioned extending through the vessel puncture and into the vessel interior. Inserting the vascular closure device 10 through the sheath 2 and attaching the latch 24 to a hub 4 of the sheath 2 positions a balloon of the vascular closure device 10 distal of a distal end 6 of the sheath 2 and within a vessel lumen 94.

FIGS. 1 and 1A illustrate the delivery tube 14 having first and second lumens 30, 32 and a balloon 34 positioned at a distal end of the delivery tube 14. The first lumen 30 includes proximal opening and a distal opening 36 at opposing ends of the delivery tube 14. The second lumen 32 includes a proximal opening and a distal opening 42. Typically, the distal opening 36 of the first lumen 30 is positioned distal of the distal opening 42 of the second lumen 32. As mentioned above, the proximal opening of the second lumen 32 is positioned in fluid communication with injection port 22 of the manifold 12. The distal opening 42 is positioned proximal of the balloon 34 at a location that permits depositing a bioadhesive sealant exterior of the vessel lumen while the balloon 34 is positioned within the vessel lumen and inflated to create a temporary seal with an inner surface of the vessel.

A distal opening of the first lumen 30 is arranged in fluid communication with an interior of the balloon 34. The proximal opening 36 of the first lumen 30 is connected in fluid communication with an interior of a housing of the balloon location device 16 and coupled in fluid communication with a source of inflation fluid 7.

An inner tube 52 of the balloon location device 16 extends through the first lumen 30 to a location distal of the balloon 34. A proximal waist 44 of the balloon 34 is connected to the delivery tube 14, and a distal waist 46 of the balloon 34 is connected to the inner tube 52 (see FIG. 3). Inflating the balloon 34 of the first lumen 30 may cause axial movement of the inner tube 52 as a shape or size of the balloon 34 changes.

The balloon location device 16 may include a housing 50, an inner tube 52, an inner tube manifold 54, an inflation manifold 56, a piston 58, and a biasing member 60. The biasing member 60 may act on the piston 58 and bias against pressure generated when delivering inflation fluid to the balloon 34. The inner tube 52 may extend completely through the housing 50 with a proximal end 65 of the inner tube 52 extending proximal of the housing 50 and a distal end 61 of the inner tube 52 extending distally through the manifold 12 an 1 delivery tube 14 to a position distal of the balloon 34 (see FIG. 3).

The inner tube 52 may define an inner tube lumen 63 (see FIG. 1A). The inner tube lumen 63 may provide a path to deliver, for example, a release member of detachable tip assembly 18, or a bioadhesive sealant to the vessel puncture. Alternatively, the inner tube lumen 63 may define a guide wire passage through which a guide wire (not shown) extends. The release member may include a filament 64 that extends through the inner tube lumen 63 and is connected to the sealing tip 62. Operating the filament 64 controls attachment and release of the sealing tip 62 relative to the inner tube 52.

The inner tube manifold 54 may be connected to the proximal end 65 of the inner tube 52. The inner tube manifold 54 may include a connection feature such as a luer lock that assists in connecting a device in fluid communication with the inner tube 52. In one example, a secondary bioadhesive sealant carrier (not shown) may be connected to the inner tube manifold 54 to deliver a secondary bioadhesive sealant through the inner tube lumen 63 to the vessel puncture to provide further sealing of the vessel puncture. The inner tube 52 is typically connected to the piston 58 so that axial movement of the inner tube 52 concurrently moves the piston 58, which movement can be seen within the housing 50 to help determine an inflation property of the balloon 34. Operation of the balloon location device 16 is shown and described with reference to U.S. Patent Application No. 61/590,000 filed on 24 Jan. 2012 and entitled BALLOON LOCATION DEVICE MANIFOLD FOR VASCULAR CLOSURE DEVICE AND METHODS, which is incorporated herein in its entirety by this reference.

Referring to FIGS. 1 and 1B, the sealing tip 62 of the detachable tip assembly 18 includes a base portion 70, a filament passage 72, a filament anchor 74, an access opening 76, and a tip securement assembly 78. The filament passage 72 is open at a proximal end of the base portion 70. The filament passage 72 provides a pathway to the filament anchor 74, which is positioned internal to base portion 70. The access opening 76 is typically positioned adjacent to the filament anchor 74 to provide an opening or access point to the filament anchor 74 to help route the filament 64 around the filament anchor 74 and into the filament passage 72. The access opening 76 may be opened on opposing sides of the base portion 70 to provide access to the filament anchor 74 from multiple locations.

The tip securement assembly 78 may include a plurality of securement members 78A-C positioned at spaced-apart locations along a length of the base portion 70. The tip securement assembly 78 may be constructed to limit movement in a distal direction, which in the context of sealing a vessel puncture includes limiting movement of the sealing tip 62 back into the vessel lumen. The first, second and third securement members 78A-C may include a tapered or sloped portion facing in a proximal direction that assists in withdrawing the sealing tip 62 from within the vessel lumen and into the vessel puncture (e.g., into a sealing material that has been deposited within and adjacent to the vessel puncture). A distal facing portion of the securement members 78A-C may have a steeper slope or taper to define a shoulder surface 79 that limits distal movement once the sealing tip 62 is positioned within the sealing material used to seal the vessel puncture.

The tip securement assembly 78 may include any desired number of securement members 78A-C. FIGS. 9-10 show an alternative sealing tip 162 that includes only first and second securement members 78A-B. The securement members 78A-C associated with sealing tips 62, 162 may be positioned at any desired location along a length of the base portion 70. For example, the securement members 78A-C may be positioned at a distal most end or proximal most end of the base portion 70, or at any location spaced between the distal and proximal ends of the base portion 70. The first and second securement members 78A-B are positioned immediately proximal and immediately distal of the access opening 76, respectively, but may be positioned at other locations in other embodiments.

The securement members 78A-C may have any desired shape and size. The securement members 78A-C shown in the figures have a relatively tow profile construction and extend around an entire circumference of the base portion 70. Other embodiments may include securement members that extend, for example, further radially outward, extend around only a portion of a circumference of the base portion 70, or include a more sharply pointed shape, such as a hook or barb shape, that provides additional anchoring and/or reduced movement in the proximal direction once lodged in the sealing material.

Figure 2B:
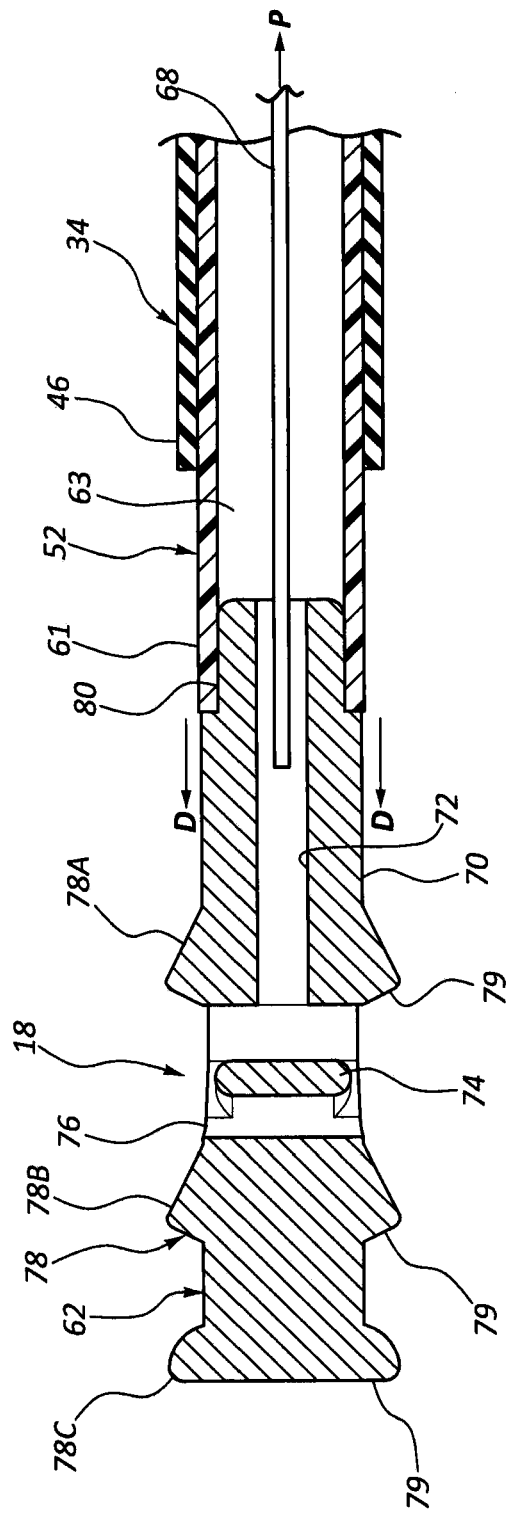
FIG. 2B is a cross-sectional view of a distal end portion of the vascular closure device of FIG. 2 taken along cross-section indicators 2B-2B.

The sealing tip 62 may also include a connection seat 80 positioned at a distal end thereof. The connection seat 80 may promote a mating interface with a distal end 61 of the inner tube 52. A portion of the sealing tip 62 may extend within the inner tube lumen 63 of the inner tube 52 and a distal normal surface of the inner tube 52 may interface with the connection seat 80 to abut against the sealing tip 62 in a distal direction. Applying a force in a proximal direction P to each of the first and second legs 66, 68 of the filament 64 draws the sealing tip 62 against the distal end 61 of the inner tube 52, as shown in FIG. 1B. Maintaining the force in the proximal direction on each of the first and second legs 66, 68 helps maintain connection of the sealing tip 62 to the vascular closure device 10. Releasing the proximally directed force P on one of the first and second legs 66, 68 unwinds the filament 64 from the filament anchor 74 as shown in FIGS. 2-2B so that the sealing tip 62 may be released from the inner tube 52 in the distal direction D (see FIG. 2B). The sealing tip 62 may be disconnected from the inner tube 52 by continuing to withdraw the inner tube 52 in the proximal direction P while the sealing tip 62 remains lodge in sealing material used to seal the vessel puncture. The tip securement assembly 78 may assist in anchoring the sealing tip 62 within the sealing material.

Referring now to FIGS. 4-8, an example method of operating a vascular closure device 10 to seal a vessel puncture 92 is shown and described. FIGS. 4-8 illustrate the vascular closure device 10 and sheath 2 extending through a vessel puncture 92 and into a vessel lumen 94 of a vessel 90. The vascular closure device 10 and sheath 2 extend through a tissue tract 98 of a tissue layer 96 to access the vessel puncture 92. The tissue tract 98 may be referred to as a percutaneous incision.

In a first operational step, a distal end 6 of the sheath 2 is advanced through the tissue tract 98 and vessel puncture 92 and into the vessel lumen 94. The vascular closure device 10 is aligned with an opening into a hub 4 of the sheath 2 for insertion into the sheath 2. Prior to inserting the vascular closure device 10 into the sheath 2, the delivery tube 14 is connected to the manifold 12, and the balloon location device 16 is advanced through the manifold 12 and delivery tube 14 and connected to a proximal end in the manifold 12.

Figure 5:
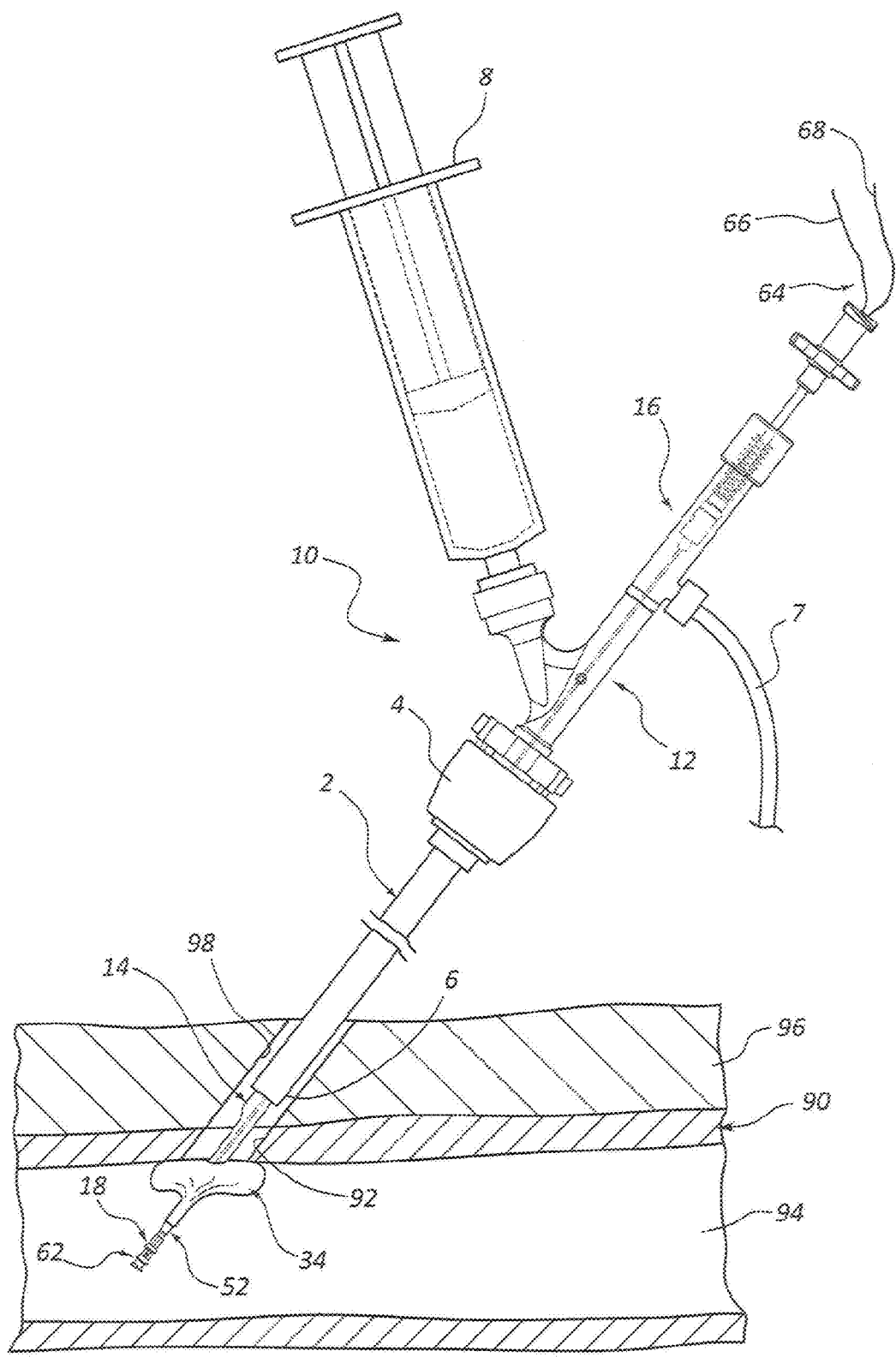

Referring to FIG. 5, the delivery tube 14 is advanced through the sheath 2 and the latch 24 is connected to the hub 4. The balloon 34 is inflated by delivering a volume of inflation fluid from the source of inflation fluid 7, through the housing 50 of the balloon location device 16, through the first lumen 30, and into the balloon 34. The vascular closure device 10 and sheath 2 are retracted (e.g., withdrawn proximally) to bring the inflated balloon 34 into contact with an inner surface of the vessel 90 adjacent to the vessel puncture 92. The inflated balloon 34 provides a temporary seal with the vessel 90 to limit blood flow through the vessel puncture 92 from within the vessel lumen 94.

Figure 6:
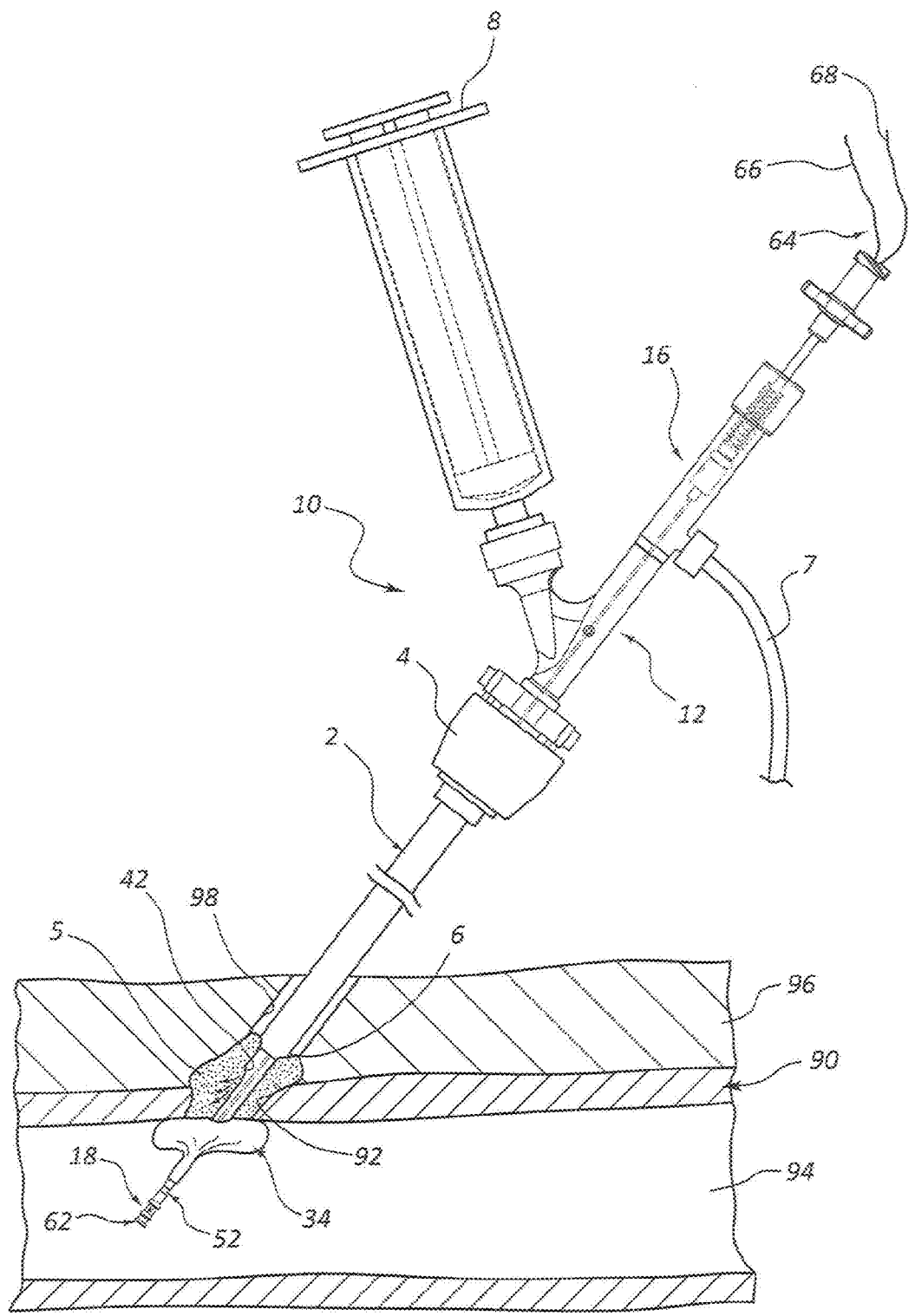
Figure 7:
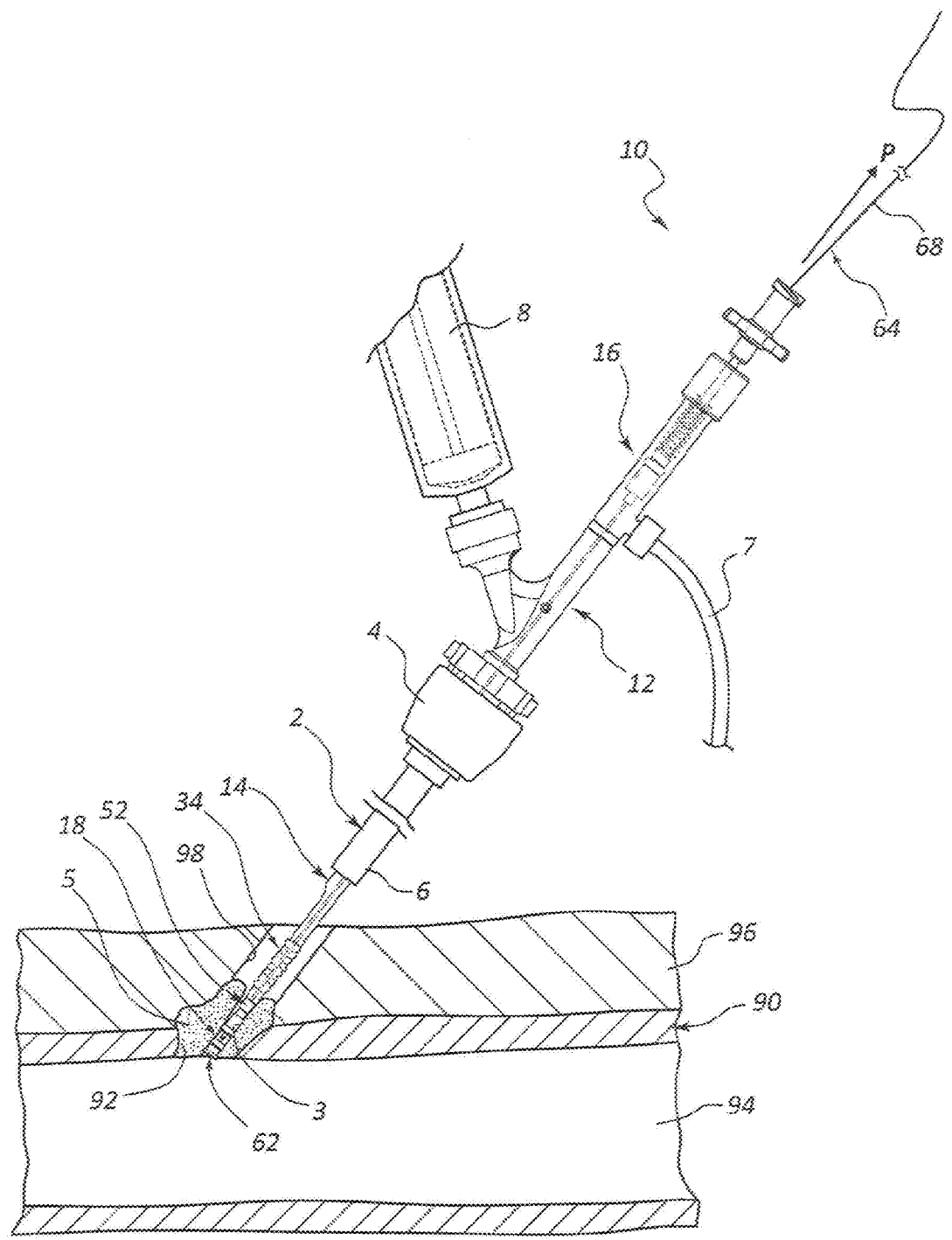

Referring to FIG. 6, a sealing material bioadhesive sealant) is delivered to the vessel puncture 92 and tissue tract 98 through a distal opening 42 of the second lumen 32. A source of sealing material may be a bioadhesive carrier 8 that is connected to the injection port 22 of the manifold 12. Operating the bioadhesive carrier 8 delivers a volume of the sealing material through the manifold 12 and second lumen 32, and out of the distal opening 42. The first sealing material forms a bioadhesive plug 5 that seals the vessel puncture 92 and tissue tract 98 from outside of the vessel 90. The sealing material may be allowed to at least partially cure into a solid or semi-solid state that limits movement of the sealing material into the vessel lumen 94 upon deflating balloon 34.

Figure 8:
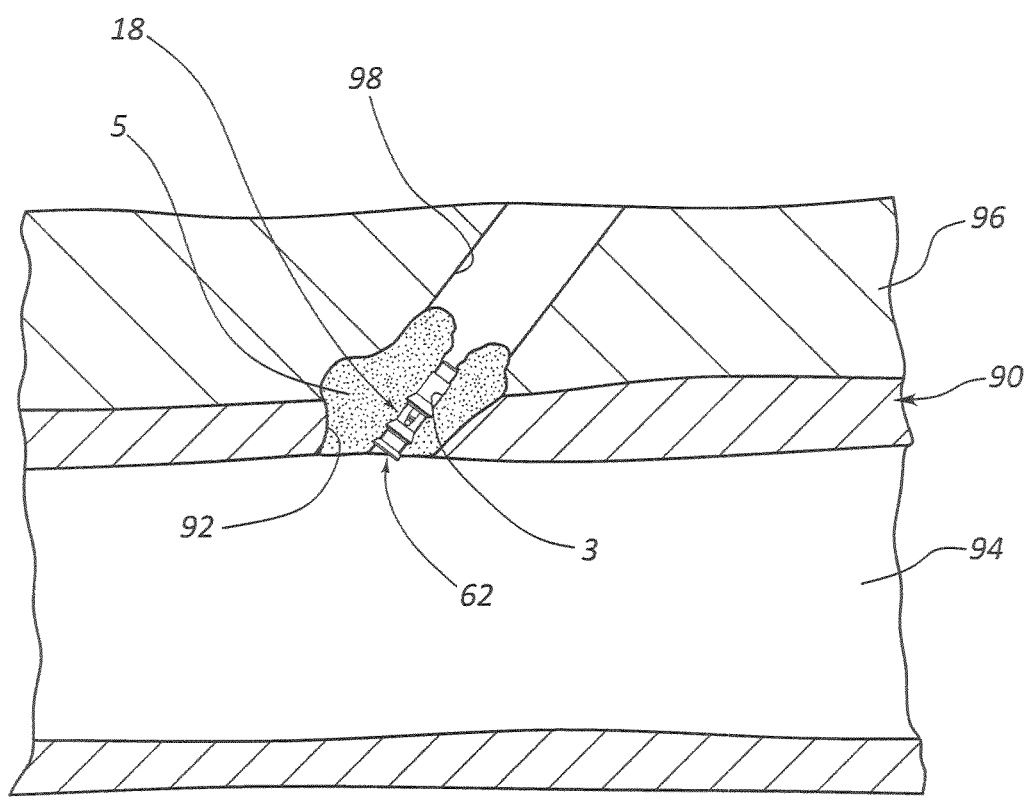

Referring to FIG. 8, the balloon 34 is deflated by withdrawing the inflation fluid through the first lumen 30, balloon location device 16, and the source of inflation fluid 7. The vascular closure device 10 and sheath 2 are further retracted (i.e., withdrawn) so that the delivery tube 14 is positioned proximal of the bioadhesive plug 5. A tract 3 may be defined within the bioadhesive plug 5 after removal of the delivery tube 14. The sealing tip 62 ma be positioned within the tract 3. The detachable tip assembly 18 may be operated to deposit the sealing tip 62 within the tract 3. The filament 64 may be unwound from the sealing tip 62 by releasing one of the first and second legs 66, 68 of the filament 64 while continuing to apply a proximally directed force to the other of the first and second legs 66, 68. Once the filament 64 is unwound from the sealing tip 62 (or at least one of the first and second legs 66, 68 is released), further retracting of the vascular closure device 10 separates the sealing tip 62 from the inner tube 52 so that the sealing tip 62 remains lodged in the tract 3 of the bioadhesive plug 5.

The sealing tip 62 may be lodged within the bioadhesive plug 5 with the tip securement assembly 78. The scaling tip 62 may help seal the vessel puncture 92 by plugging or sealing a passage through the bioadhesive plug 5 that is otherwise present upon removal of the vascular closure device 10 from the vessel puncture 92. The sealing tip 62 may comprise a bioresorbable material. The sealing tip 62 may comprise a material such as, for example, collagen.

The sealing tip 62 may be released from the vascular closure device 10 using a low or no tensile force release member (e.g., filament 64), which may also be referred to a low or no tensile release device or method. The tensile force involved with releasing the sealing tip 62 from the vasculur closure device 10 may be relatively small as compared to other types of release mechanisms that require disconnecting a mechanical fastener, breaking apart an attachment feature, or other relatively high tensile force release device or method. In one example, the amount of force required is less than 1 lb., and preferable less than 0.5 lbs.

While the amount of force needed to release the sealing tip 62 is relatively low, an amount of force that may be applied to maintain connection of the sealing tip 62 to the vascular closure device 10 during all operational steps up to the point of releasing the sealing tip 62 may be relatively high. For example, relatively high axial force may be applied to the first and second legs 66, 68 of the filament 64 to maintain connection of the sealing tip 62 to the inner tube 52 until the operator decides to release the sealing tip 62 within the bioadhesive plug 5. Tension in the first and second legs 66, 68 may be applied and maintained by securing the first and second legs 66, 68 to, for example, the inner tube manifold 54 or other device positioned at a proximal end of the balloon location device 16. In some arrangements, an operator may manually grasp at least one of the first and second legs 66, 68 to maintain a desired amount of tension that retains the sealing tip 62 until the operator chooses to release one of the first and second legs 66, 68 to unwind the filament 64 from the sealing tip 62.

Referring now to FIGS. 11-13, another example sealing tip 262 is shown and described. The sealing tip 262 comprises a two-piece design. The two pieces are initially assembled together. Relative movement between portions of the two pieces once assembled together causes one of the pieces to expand radially outward to act as an anchor or strut.

The sealing tip 262 includes a base portion 270 and a tip securement member 278. The base portion 270 is inserted into the tip securement member 278. The sealing tip 262 may be connected to the inner tube 52 of the vascular closure device 10 with a proximal end of the base portion 270 extending into the inner tube 52 and a distal end surface of the tip securement member 278 abutting against a distal end surface of the inner tube 52.

The base portion 270 may include a filament passage 272, a filament anchor 274, and an access opening 276. The filament 64 may extend through the filament passage 272 and wrap around the filament anchor 274. The access opening 276 may provide access to the filament anchor 274 for purposes of, for example, threading the filament around the filament anchor 274 and into the filament passage 272.

The base portion 270 may also include an attachment member 281. The attachment member 281 may be constructed as a protrusion that extends radially outward from an outer circumferential surface of the base portion 270. The attachment member 281 may be arranged and configured to mate with an aperture formed in an outer circumferential surface of the tip securement member 278. The attachment member 281 may provide a positive attachment between the base portion 270 and tip securement member 278. The attachment member 281 may include a tapered construction that permits easier assembly of the base portion 270 and tip securement member 278 to each other.

The tip securement member 278 may include a distal portion 282, a proximal portion 284, a plurality of expandable members 286A-13, and a plurality of cutouts 289A-B. An tent aperture 287 may be formed in a distal portion 282 sized to receive the attachment member 281. A stop surface 288 may be positioned at a proximal end of the proximal portion 284 and arranged to abut against a distal end surface of die inner tube 52 (see FIG. 13). The cutouts 289A-B may define, at least in part, the expandable members 286A-B. The expandable members 286A-B may be configured to expand radially outward upon application of an axial force to the tip securement member 278. FIG. 12 shows the tip securement member 278 in an expanded position. The tip securement member 278 may be moved into the expanded position by applying a force to the base portion 270 in the proximal direction P using the filament 64 while maintaining an axial position of the inner tube 52, which is abutting against the proximal surface stop surface 288 of the tip securement member 278.

The sealing tip 262 may be operated into the expanded position shown in FIG. 12 after positioning the sealing tip 262 within the tissue puncture e.g., within a sealing material disposed adjacent to the vessel puncture to seal the venture puncture). In some arrangements, the sealing tip 262 may be operable without use of the attachment member 281 in attachment aperture 287. The base portion 270 and tip securement member 278 may be held in place axially relative to each other once the sealing tip 262 is assembled with the inner tube 52. The attachment member 281 may assist in maintaining assembly of the sealing tip 262 prior to mounting the sealing tip 262 with the remainder of the vascular closure device 10.

Referring now to FIGS. 14 and 15, an alternative sealing tip 362 is shown and described. The sealing tip 362 includes a tip securement member 378 that has four expandable members 386A-D. The sealing tip 362 includes a base portion 370 having a filament passage 372, a filament anchor (not shown, but within base portion 370), an access opening (not shown, but included within base portion 370), and an attachment member 381. The tip securement member 378 includes a distal portion 382 having an attachment aperture 387, a proximal portion 384 having a stop surface 388, expandable members 386A-C, and a plurality of cutouts 389.A-B (additional cutouts being hidden from view). Once assembled together, relative axial movement of the base portion 370 while maintaining an axial position of the tip securement member 378 moves the expandable members 386A-C into the expanded position shown in FIG. 15. The expandable members 386A-C may act as anchors or struts that maintain an axial position of the sealing tip 362 within a sealing material (e.g., bioadhesive plug 5) after the sealing tip 362 is detached from the vascular closure device 10.

Referring now to FIGS. 16 and 17, another example sealing tip 462 is shown and described. The sealing tip 462 comprises a single piece design with a plurality of expandable members. The sealing tip 462 includes abuse portion 470 and a tip securement member 478 that includes a plurality of expandable members 486A-B. The base portion 470 includes a filament passage 472, a filament anchor 474, an access opening 476, and a connection seat 480. A plurality of cutouts 489 are formed in the base portion 470 and define at least in part in the expandable members 486A-B.

The filament passage 472 provides a pathway for a filament 64 to extend through the sealing tip 462 and wrap around the filament anchor 474. The access opening 476 may provide access to the filament anchor 474 for routing the filament 64 around the filament anchor 474 and into the filament passage 472.

The connection seat 480 may be configured to interface with a distal end portion of an inner tube 52 of the vascular closure device 10. A proximal portion of the base portion 470 may extend into the inner tube 52 while the connection seat 480 may abut against a distal end surface of the inner tube 52 as shown in FIGS. 16 and 17. Applying a force in a proximal direction P to the first and second legs 66, 68 of the filament 64 while maintaining an axial position of the inner tube 52 causes the expandable members 486, B to expand radially outward as shown in FIG. 17. Once moved into the radially outward expanded position as shown in FIG. 17, the expandable members 486.A-B may maintain the expanded position after releasing tension in the filament 64. The same principle of the expandable members maintaining their expanded position may apply to all thereat embodiments disclosed herein.

Once the expandable members 486A-B are moved into the expanded position shown in FIG. 17, the operator may release tension on one of the first and second legs 66, 68 while continuing to apply the proximally directed force to the other of the first and second legs 66, 68 to unwind the filament 64 from the filament anchor 474. Once the filament 64 is unwrapped or disconnected from the filament anchor 474, the sealing tip 462 may be detached from the vascular closure device 10. The sealing tip 462 may automatically disconnect from the vascular closure device upon release of the proximally directed force to one of the first and second legs 66, 68. In some arrangements, the sealing tip 462 detaches only upon application of a withdrawal force to the vascular closure device 10 after releasing one of the first and second legs 66, 68. The filament 64 may unwrap from the sealing tip 462 as the vascular closure device 10 is withdrawn proximally and the expandable members 486A-B maintain the sealing tip 462 within the sealing material (e.g., bioadhesive 5).

The sealing materials discussed herein may comprise a single component, or may comprise multiple sealant components that are mixed together. The multiple sealant components may further react together to form a crosslinked network. The sealant components may be naturally derived or synthetic. Some example synthetic components include polykthers such as polyethyle glycol, polypropylene glycol and polytetrahydrofuran. Other examples of synthetic components may include polyamine compositions such as polyvinylpyrrolidones, polyethylene imines and hydrogenated polyacrlonitriles. Other example sealant components include polyacrylic and methacrylic compounds such as polyacrytic acid. Example naturally derived components include protienaceous compositions such as albumin, collagen and polylysine. Other examples include carbohydrate compositions such polyhyaluronic acid. The sealant components may also contain reactive functional groups to promote chemical crosslinking. The sealant components may be cross-linked by any known method including, for example, condensation reactions, Michael addition, and free radical. Functional groups used for cross-linking may include, for example, thiols, acrylates, amines, succinimydyls and aldehydes, to name a few.

While this invention has been described with reference to certain specific embodiments and examples, it will be recognized by those skilled in the art that many variations are possible without departing from the scope and spirit of this invention. The invention, as defined by the claims, is intended to cover all changes and modifications of the invention which do not depart from the spirit of the invention.

What is claimed is:

1. A vascular closure system, comprising:
   a delivery tube;
   an inner tube having a distal-most end surface, the inner tube positioned within the delivery tube;
   an expandable anchor directly connected to the delivery tube and temporarily positionable through a vessel puncture within a vessel;
   a sealing material positionable outside of the vessel and configured to seal the vessel puncture;
   a detachable sealing tip assembly comprising:
      a sealing tip positioned on the inner tube distal of the expandable anchor, the sealing tip abutting the distal-most end surface of the inner tube, the sealing tip being releasable from the inner tube within the sealing material upon removal of the anchor and sealing tip through the sealing material;

the sealing tip having a distal end portion, a proximal end portion, and midsection positioned between the distal and proximal end portions, the midsection having a filament anchor, the proximal end portion having an internal passage, the internal passage terminating proximal to the distal end portion; and a sealing tip release member operable to release the sealing tip without application of a tactile force, wherein the sealing tip release member includes a filament slidably threaded around the filament anchor of the sealing tip and extending within the external passage and proximally from the sealing tip, the filament being operable to unwind from the sealing tip to release the sealing tip from the vascular closure device to seal the vessel puncture after removal of the anchor from the vessel puncture wherein the sealing tip includes a base portion and a tip securement portion, and relative axial movement between the base portion and the tip securement portion expands the tip securement portion.

2. A vascular closure system according to claim 1, wherein the expandable anchor comprises an expandable balloon structure.

3. A vascular closure system according to claim 1 wherein the sealing tip includes a bioresorbable material.

4. A vascular closure system according to claim 1, wherein the sealing material is a bioadhesive, and removal of the expandable anchor through the sealing material forms a tract through the sealing material that is filled with the sealing tip.

5. A vascular closure system according to claim 1, wherein the tip securement portion extends radially outward from the base portion to anchor the sealing tip.

6. The vascular closure system of claim 1, wherein a portion of the expandable anchor is connected to the inner tube.

* * * * *